(12) United States Patent
Rezachek et al.

(10) Patent No.: US 8,939,006 B2
(45) Date of Patent: Jan. 27, 2015

(54) PHOTOACOUSTIC DETECTOR WITH LONG TERM DRIFT COMPENSATION

(75) Inventors: Thomas M. Rezachek, Cottage Grove, MN (US); Gary P. Shubinsky, Buffalo Grove, IL (US); Michael Freeman, Northville, MI (US)

(73) Assignee: Honeywell International Inc., Morristown, NJ (US)

( * ) Notice: Subject to any disclaimer, the term of this patent is extended or adjusted under 35 U.S.C. 154(b) by 238 days.

(21) Appl. No.: 13/100,998

(22) Filed: May 4, 2011

(65) Prior Publication Data

US 2012/0279279 A1 Nov. 8, 2012

(51) Int. Cl.
*G01N 21/00* (2006.01)
*G01N 21/17* (2006.01)

(52) U.S. Cl.
CPC .................. *G01N 21/1702* (2013.01)
USPC ............ 73/1.06; 73/23.21; 73/31.05; 73/579; 73/584; 73/646; 73/649; 702/87; 702/103; 702/105; 356/437

(58) Field of Classification Search
USPC ............. 73/1.01–1.89, 1.01–1.89; 250/252.1; 702/85–107, 22–32; 356/432–442
See application file for complete search history.

(56) References Cited

U.S. PATENT DOCUMENTS

| | | | | |
|---|---|---|---|---|
| 5,841,017 A * | 11/1998 | Baraket et al. | ................. | 73/1.59 |
| 6,006,585 A * | 12/1999 | Forster | ........................ | 73/24.01 |
| 6,031,233 A * | 2/2000 | Levin et al. | ............. | 250/339.11 |
| 6,662,627 B2 * | 12/2003 | Arnott et al. | ................. | 73/24.02 |
| 6,843,102 B1 * | 1/2005 | Shulga et al. | ................. | 73/25.01 |
| 7,428,044 B2 * | 9/2008 | Vuong et al. | ................. | 356/243.1 |
| 7,586,611 B2 * | 9/2009 | Lowney et al. | ............... | 356/432 |
| 7,886,576 B2 * | 2/2011 | Uber | ........................... | 73/24.02 |
| 8,379,206 B2 * | 2/2013 | Kachanov et al. | ............ | 356/436 |
| 8,441,644 B2 * | 5/2013 | Kachanov et al. | ............ | 356/436 |
| 2002/0146136 A1 * | 10/2002 | Carter, Jr. | ........................ | 381/59 |
| 2002/0194897 A1 * | 12/2002 | Arnott et al. | ................. | 73/23.31 |
| 2005/0121614 A1 | 6/2005 | Stuttard | ........................ | 250/343 |
| 2007/0229834 A1 * | 10/2007 | Patel et al. | ..................... | 356/432 |
| 2009/0320561 A1 | 12/2009 | Fritz et al. | ..................... | 73/24.02 |
| 2010/0007889 A1 * | 1/2010 | Van Kesteren | ................ | 356/436 |
| 2010/0027012 A1 | 2/2010 | Fritz et al. | ..................... | 356/432 |
| 2010/0045998 A1 | 2/2010 | Fritz et al. | ..................... | 356/450 |
| 2010/0147051 A1 | 6/2010 | Tobias | ......................... | 73/24.02 |
| 2010/0242572 A1 * | 9/2010 | Yu | ................................. | 73/24.02 |
| 2011/0214479 A1 * | 9/2011 | Kachanov et al. | ........... | 73/24.02 |

(Continued)

FOREIGN PATENT DOCUMENTS

DE 19516974 A1 * 10/1996
EP 0855592 A1 * 7/1998

OTHER PUBLICATIONS

English Translation of DE 19516974 A1 Dated Oct. 1996.*

(Continued)

*Primary Examiner* — Hezron E Williams
*Assistant Examiner* — Alexander Mercado
(74) *Attorney, Agent, or Firm* — Husch Blackwell LLP

(57) ABSTRACT

A photoacoustic detector wherein control circuits compensate for long term variations of components therein including a light source and sensing microphones. The control circuits intermittently energize the source to evaluate changes in at least source resistance. The control circuits intermittently energize an acoustic generator to evaluate changes in one or more generator responsive microphones.

18 Claims, 2 Drawing Sheets

(56) References Cited

U.S. PATENT DOCUMENTS

2011/0214481 A1* 9/2011 Kachanov et al. ............ 73/24.02
2011/0216311 A1* 9/2011 Kachanov et al. ............. 356/213
2012/0188555 A1* 7/2012 Izatt et al. ..................... 356/479
2012/0197575 A1* 8/2012 Saveliev et al. ............... 702/104
2012/0281271 A1* 11/2012 Sandstrom et al. ........... 359/305
2013/0057946 A1* 3/2013 Kirkby et al. ................. 359/310

OTHER PUBLICATIONS

English Translation of EP 0855592 A1 Dated Jul. 1998.*

* cited by examiner

PHOTOACOUSTIC DETECTOR WITH LONG TERM DRIFT COMPENSATION

FIELD

The application pertains to photoacoustic detectors. More particularly, the application pertains to such detectors which include circuitry for carrying out long term drift compensation.

BACKGROUND

Various types of photoacoustic sensors are known to detect gases. These include, Fritz et al., US Patent Application No. 2009/0320561, published Dec. 31, 2009 and entitled "Photoacoustic Cell"; Fritz et al., US Patent Application No. 2010/0027012, published Feb. 4, 2010 and entitled, "Photoacoustic Spectroscopy System"; Fritz et al., US Patent Application No. 2010/0045998, published Feb. 25, 2010 and entitled "Photoacoustic Sensor"; and Tobias, US Patent Application No. 2010/0147051, published Jun. 17, 2010 and entitled, "Apparatus and Method for Using the Speed of Sound in Photoacoustic Gas Sensor Measurements. The above noted published applications have been assigned to the assignee hereof, and are incorporated herein by reference.

Precise and repeatable performance of photoacoustic detectors is preferred. Changes in detector response over a period of time can result in measurements exhibiting variances from those initially determined during manufacture and initial calibration. In some instances this can result in the respective detector drifting out of specification.

User calibration is a partial solution to detector drift. However, not all users have the ability or interest required to carry out field calibration.

DETAILED DESCRIPTION

Figure 1:
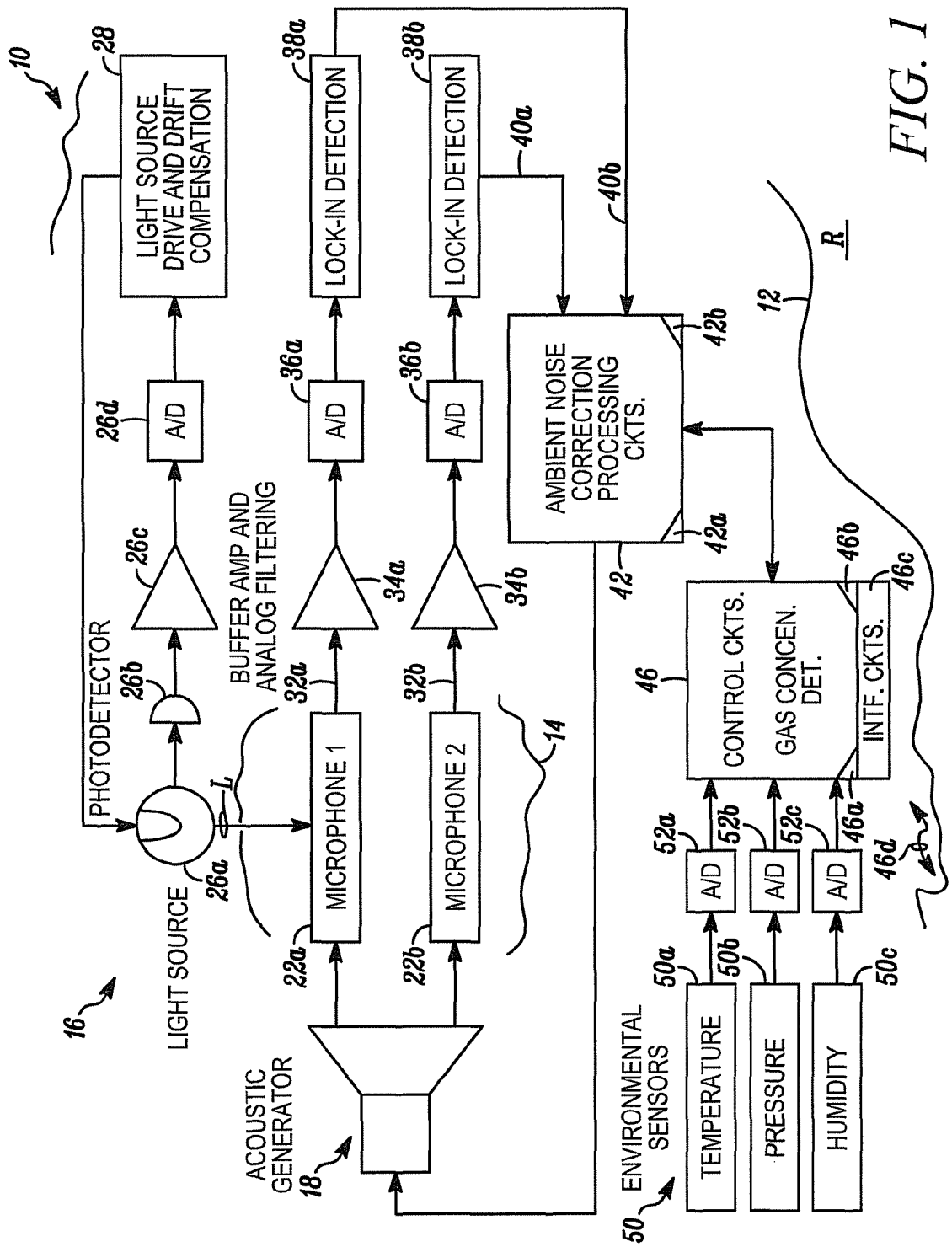
FIG. 1 is a block diagram of a detector in accordance herewith.

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

The long term drift in a photoacoustic (PA) sensor is primarily due to changes in elements that can wear or degrade over time, for example, the light source (lamp), and the PA microphones. Methods are described below for detecting and compensating for long term changes in the light source and one or more microphones of a photoacoustic sensor. An acoustic generator operating at multiple frequencies to monitor the long-term drift of the sensor's microphones as well as the photoacoustic cavity's membrane and pressure sealing elements. The long term drift of the light source can be monitored and corrected for by measuring source electrical resistance and optical output.

FIG. 1 is a block diagram of an exemplary detector 10 in accordance herewith. It will be understood that the detector 10 is exemplary only. Other detectors come within the spirit and scope hereof.

The detector 10 can monitor concentrations of one or more airborne gases in an adjacent region R. Detector 10 includes a housing 12 which can carry a photoacoustic sensing chamber or cell 14.

Detector 10 includes a radiant energy emitting and control system 16 and an acoustic generator 18. Dual microphones 22 a, b are carried by or adjacent to the chamber 14 and respond to inputs from generator 18. The microphones 22 a, b also respond to audio generated by radiant energy, or light L, from a source 26a.

The source 26a injects light into the chamber 14 as would be understood by those of skill in the art to produce a photoacoustic audio signal, and need not be discussed further. The source 26a can emit infra-red radiant energy.

Feedback is provided in system 16 by a photodetector 26b which couples a signal, indicative of the output of source 26a through an amplifier and filter 26c, via an analog-to-digital converter 26d to drive and drift compensation circuits 28.

Dual channel output signals on lines 32 a, b from the microphones 22 a, b can be coupled via amplifiers 34 a, b to analog-to-digital converters 36 a, b to lock-in detection circuits 38 a, b. Output signals on lines 40 a, b from the detection circuits 38 a, b can be coupled to ambient noise correction processing circuits 42. Processing circuits 42 can be implemented with one or more programmable processors 42a which execute software or control programs 42b pre-stored on computer readable media such as semiconductor memory chips.

The corrected outputs can be coupled to control and processing circuits 46 which can carry out gas concentration detection. Circuits 46 can be implemented with one or more programmable processors 46a which execute software or control programs 46b pre-stored on computer readable media such as semiconductor memory chips. Using pre-stored instructions, such as 42b, baseline and span corrections can be carried out as explained below.

Interface circuits 46c, also coupled to the control circuits 46 provide for bidirectional communication with a docking station, or, a displaced monitoring system via a wired or wireless medium 46d. Environmental sensors 50a, b, c can detect ambient temperature, pressure or humidity in the vicinity of the housing 12. Signals from the sensors 50a, b, c can be digitized in analog-to-digital converters 52a, b, c and the coupled to the control circuits 46 as discussed above.

Further, closed loop control system 16, which can include the infra-red emitter of radiant energy, source 26a, can sense emitted radiant energy intensity, or amplitude, via detector 26b. The system 16 compensates for drift in output of the radiant energy source 26a.

The detector 10 can be calibrated at manufacture. A detector response transfer function can be established at initial calibration. Characteristics of the initial transfer function can be stored by control circuits 46 for subsequent use.

Subsequently, in one embodiment, the intensity of the infra-red source 26a can be varied while measuring the cell output signal. An updated transfer function can be established and compared to the stored transfer function. Span and baseline correction values can be determined using the original and current transfer functions. The correction values can also be stored by control circuits 46 for subsequent use in compensating gas concentration values.

Figure 2A:
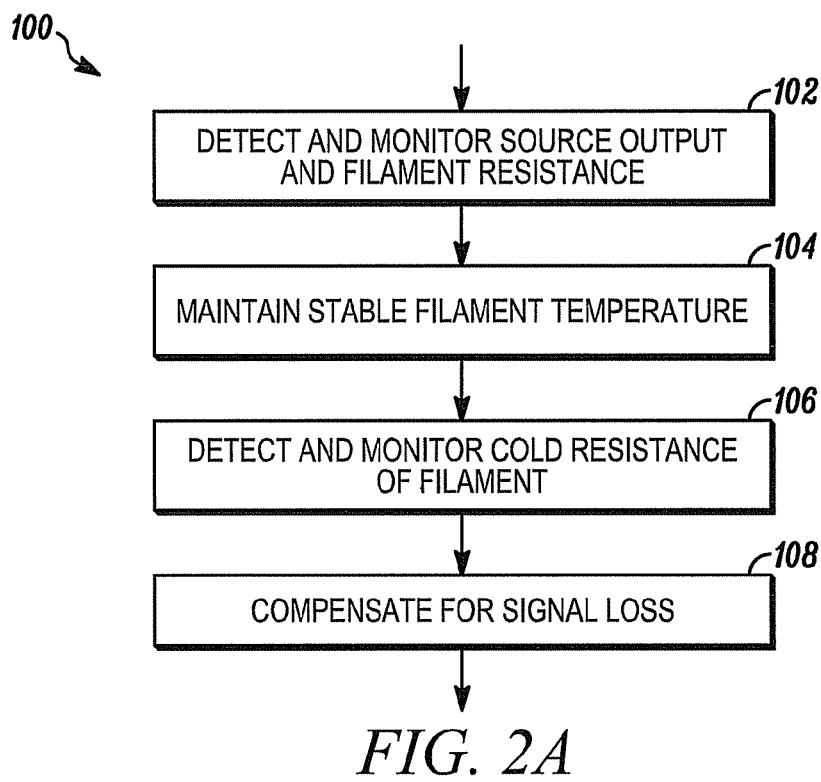
FIGS. 2A, 2B are flow diagrams of compensation methods usable with the detector of FIG. 1.

A method 100, of lamp degradation monitoring and compensation, is illustrated in FIG. 2A. The radiant energy output of the source 26a can be monitored, constantly or intermittently using a silicon photodiode, or other optical sensor, such as 26b, and by measuring the lamp filament resistance as at 102. Since the change in resistance of a tungsten filament with temperature is well known, measuring the filament resistance will enable the filament temperature to be determined if the filament resistance at any given temperature is known. The latter condition can be satisfied by simply measuring the filament resistance after turning the lamp off for several seconds and using a local ambient temperature sensor, such as sensor 50a.

The lamp monitoring photodiode signal, from sensor 26b, and the filament resistance will vary as the lamp power is modulated at the operating frequency of the detector 10 (typically 7 or 11 Hz), so their values at several points in the modulation cycle will need to be acquired. In order to assure that the calibration of the PA detector 10 remains valid, the drive power to the filament of the source 26b can be slowly adjusted as to keep the filament temperature as stable as possible, and thus maintain the same radiance spectrum at 104.

The cold resistance (lamp off for several seconds) of the filament of source 26b can also be periodically measured as at 106, to monitor tungsten loss from the filament. This provides monitoring of any IR output loss due to tungsten deposition on the glass bulb of source 26b. This measurement can be made in combination with the output of photodiode 26b to determine the extent of the tungsten deposition on the glass bulb. Any loss of IR signal at a given filament temperature would be compensated for, as at 108, by increasing the processed (ambient noise corrected) PA microphone signal value just prior to the control circuits 42 using that value to compute a current CO2 concentration.

Figure 2B:
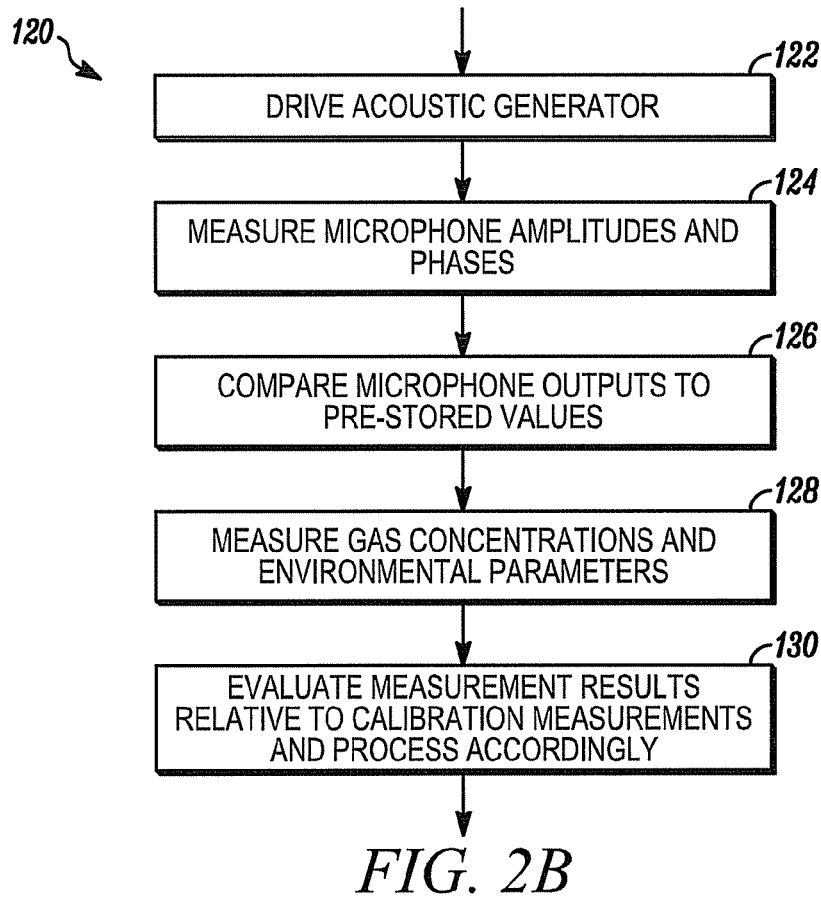

An onboard acoustic generator 18 can be used to track the absolute signal levels 32a,b of the two PA microphones 22a,b over time and at several frequencies selected based on the fundamental performance characteristic of microphones. Therefore, drift in the PA microphones 22a,b can be detected and compensated for, as in FIG. 2B, method 120.

The acoustic generator 18 can be driven at a predetermined target frequency, as at 122, and allowed to stabilize prior to measuring the signal amplitude and phase of both microphones 22a,b using lock-in detection 38a,b over several complete cycles (the PA lamp 26a would not be modulated during this measurement), as at 124. Several frequencies could be sequentially measured in this manner (for example 7, 14, 28, 55, and 110 Hz) and then the detector 10 would return to normal operation.

The response of microphone to all of these frequency stimulants can be measured and compared by the circuits 42, as at 126, to the initial performance of the microphones 22a,b. The CO2 concentration before and after this measurement and the environmental conditions during it (pressure, temperature, and relative humidity) could be monitored, as at 128, to assure that nothing had changed significantly during the calibration measurements. If significant changes were found, the calibration data could be discarded, as at 130. The time points selected for this procedure could be selectively chosen to occur at certain times of the day or night or when the environmental conditions were especially appropriate.

The data obtained from the calibration procedure 120 could be accumulated and stored for an extended period, for example in flash memory-type storage, and could be used to detect changes over time in the response of both microphones 22a,b, their respective membranes, leaks in the PA chamber 14 due to the failure of sealing elements, or changes in output of the acoustic generator 18 used for the calibration. In general, changes in amplitude or phase common to both microphones 22a,b would be assumed to be due to changes in the output of the acoustic generator 18.

In the acoustic generator 18, where amplitude changes at all frequencies used in the calibration can be expected to track together the average of each microphone over all frequencies tested could be used to compute the change in acoustic generator amplitude. Further, leaks in the PA chamber 14 or associated membranes would cause a frequency dependent change in microphone amplitude. Slow leaks would cause the low frequency calibration response to increase, but not the high frequency response.

The magnitude of the PA microphone signals 32a,b in response to increases at the normal PA operating frequency could be used to compensate for the corresponding increase in PA cavity loss at that frequency. Larger leaks in the PA chamber 14 would lead to substantial increases at all frequencies, but would also probably render the PA detector 10 inoperable (the leaks would be too large to compensate). Changes in the microphone response over time could also be detected using this technique. Given that all the frequencies typically track together, the high frequency response can be used to track microphone gain changes and the low frequency response can be used to track PA cavity leaks.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. A photoacoustic detector comprising:
    a sensing chamber;
    a source which directs radiant energy into the chamber;
    at least one microphone, coupled to the chamber, to detect acoustic events therein;
    an acoustic generator coupled to the chamber; and
    control circuits coupled to the source, the acoustic generator and the at least one microphone,
    wherein the control circuits compensate for output loss from the source and changes in the at least one microphone,
    wherein the acoustic generator is used by the control circuits to track an absolute signal level of the at least one microphone over time and at several frequencies that are selected based upon a fundamental performance characteristic of the at least one microphone,
    wherein the several frequencies are sequentially measured by driving the acoustic generator at a predetermined target frequency prior to measuring a response of the at least one microphone including a signal amplitude and phase over several complete cycles, and
    wherein the response of the at least one microphone to the several frequencies is compared by the control circuits with an initial performance of the at least one microphone to detect changes over time.

2. A detector as in claim 1 which includes source related circuitry to electrically drive the source.

3. A detector as in claim 2 where the source related circuitry includes a closed loop radiant energy control system.

4. A detector as in claim 3 where the closed loop radiant energy control system includes an infra-red emitter oriented to direct infra-red radiant energy into the sensing chamber and an optical sensor to provide feedback.

5. A detector as in claim 2 where the control circuits are coupled to the at least one microphone, where the control circuits receive a first electrical signal from the at least one microphone and including processing circuits, which, over a predetermined time interval, process the first electrical signal from the at least one microphone to increase the signal-to-noise ratio thereof.

6. A detector as in claim 5 where the at least one microphone includes a second microphone carried adjacent to the chamber and where the processing circuits process a second electrical signal, from the second microphone.

7. A detector as in claim 6 which includes additional circuitry to eliminate a noise component from the processed signals.

8. A detector as in claim 6 wherein first and second ambient noise corrected signals are obtained from the first and second electrical signals, and further including confirmation circuitry to determine that the first and second ambient-noise corrected signals exhibit a constant amplitude ratio and a fixed phase relationship, and which responsive thereto, generate an indicium indicative thereof.

9. A detector as in claim 2 where the control circuits include filament resistance detection circuits.

10. A detector as in claim 2 which includes an ambient temperature sensor coupled to the control circuits.

11. A detector as in claim 10 where the control circuits include additional circuitry to evaluate a resistance value of the source at an ambient temperature and to compensate the at least one microphone for the output loss from the source.

12. A detector as in claim 11 where the control circuits, responsive to the evaluated resistance value, compensate for the changes in the at least one microphone.

13. A detector as in claim 1 where the response of the at least one microphone is compared to pre-stored values.

14. A detector as in claim 13 where the pre-stored values include initial calibration values.

15. A method of compensating a photoacoustic detector comprising:
   providing a photoacoustic detector;
   calibrating the detector, and obtaining an initial transfer function indicative of detector response;
   storing the transfer function;
   exposing the detector to airborne ambient conditions and determining at least one gas concentration;
   obtaining another transfer function for the detector subsequent to the exposing;
   comparing the initial and the another transfer functions;
   responsive to the comparing, establishing at least one compensating indicium for the detector; and
   carrying out measurements and compensating performance of the detector for output loss from a radiant energy source and changes in an acoustic generator, carried in the detector, wherein the initial transfer function is based upon a measurement of an absolute signal level of the acoustic detector over time and at several frequencies that are selected based upon a fundamental performance characteristic of the acoustic detector, wherein the several frequencies are sequentially measured by driving the acoustic generator at a predetermined target frequency prior to measuring a response of the acoustic detector including a signal amplitude and phase of the acoustic detector over several complete cycles, and wherein the response of the acoustic detector to the several frequencies is compared by the control circuits with the initial transfer function of the acoustic detector to detect changes over time.

16. A multi-channel photoacoustic detector comprising:
   a multi-channel photoacoustic sensing cell which has first and second acoustic output channels;
   an acoustic generator coupled to the cell;
   a source of radiant energy coupled to the cell and which includes a closed loop control system to at least intermittently energize the source of radiant energy; and
   control circuits, coupled to the output channels, the generator and the source, wherein the control circuits compensate for output loss from the source and changes in the acoustic generator, wherein the acoustic generator is used by the control circuits to track an absolute signal level of at least one microphone over time and at several frequencies that are selected based upon a fundamental performance characteristic of the at least one microphone, wherein the several frequencies are sequentially measured by driving the acoustic generator at a predetermined target frequency prior to measuring a response of the at least one microphone including a signal amplitude and phase over several complete cycles, and wherein the response of the at least one microphone to the several frequencies is compared by the control circuits with an initial performance of the at least one microphone to detect changes over time.

17. A detector as in claim 16 where the control circuits store at least one sensing cell transfer function to enhance a signal-to-noise ratio thereof and to make a gas concentration determination based thereon.

18. A detector as in claim 17 which includes periodic actuation circuitry to drive the acoustic generator and produce acoustic outputs in the cell to calibrate at least one acoustic sensor in one of the output channels.

* * * * *